United States Patent [19]
Sturla et al.

[11] Patent Number: 5,830,440
[45] Date of Patent: *Nov. 3, 1998

[54] AQUEOUS AEROSOL HAIR SPRAY

[75] Inventors: Jean-Michel Sturla, Suresnes; Régis Beitone, Paris, both of France

[73] Assignee: L'Oreal, Paris, France

[*] Notice: The term of this patent shall not extend beyond the expiration date of Pat. No. 5,

[21] Appl. No.: 467,808

[22] Filed: Jun. 6, 1995

Related U.S. Application Data

[63] Continuation of Ser. No. 90,106, filed as PCT/FR92/01081, Nov. 20, 1992 published as WO93/09757, May 27, 1993, abandoned.

[30] Foreign Application Priority Data

Nov. 21, 1991 [FR] France .................................. 91 14353

[51] Int. Cl.$^6$ ...................................................... A61K 7/11
[52] U.S. Cl. ...................... 424/47; 426/70.1; 426/78.02; 426/70.9; 426/70.12; 426/70.14; 426/70.6; 426/DIG. 1; 426/DIG. 2; 426/70.11; 514/957
[58] Field of Search ........................ 424/45, 47, DIG. 1, 424/DIG. 2, 70.11, 70.1, 78.02, 70.9, 70.12, 70.14, 70.6; 514/957

[56] References Cited

U.S. PATENT DOCUMENTS

| Re. 34,157 | 1/1993 | Sramek | 424/71 |
|---|---|---|---|
| 3,914,403 | 10/1975 | Valan | 424/47 |
| 4,543,249 | 9/1985 | Nelson | 424/DIG. 1 |
| 4,874,604 | 10/1989 | Sramek | 424/47 |
| 4,954,336 | 9/1990 | Chuang et al. | 424/71 |
| 5,053,218 | 10/1991 | Shernov | 424/47 |
| 5,286,477 | 2/1994 | Bhatt et al. | 424/47 |

FOREIGN PATENT DOCUMENTS

| 0 418 676 | of 0000 | European Pat. Off. |
|---|---|---|
| 0 523 388 | of 0000 | European Pat. Off. |
| 0418676 | 3/1991 | European Pat. Off. |
| 1 541 599 | of 0000 | France |
| 1 617 685 | of 0000 | Germany |
| 30 07 334 | of 0000 | Germany |
| 31 38 298 | of 0000 | Germany |
| 33 20 976 | 6/1983 | Germany |

OTHER PUBLICATIONS

J. Guth et al, "Addressing the North American Trend Toward Low VOC Hair Sprays", Seifen Öle, Fette, Wachse, vol. 117, No. 13, Aug. 1991, pp. 464–467.
Oteri, R. et al. (1991). Cosmetics & Toiletries, vol. 106, pp. 29–34.
Cosmetics and Toiletries, vol. 106, pp. 29–34 (1991).
Seifen–Ole–Fette–Wachse, 117, Jahrgang, Nr. 13 pp. 485–486 (1991).
Seifen–Ole–Fette–Wachse, 117, Jahrgang, Nr. 13, pp. 464–467 (1991).
Schrader, "Grundlagen und Rezepturen der Kosmetika", Huthig Buch Verlag, Heidelberg, p. 780 (1989).
Fey.Otte, Worterbuch der Kosmetik, 3. Auflage, Wissenschaftliche Verlagsgesellschaft mbH, Stuttgart, pp. 286–287 (1991).
Schrader, "Grundlagen und Rezepturen der Kosmetika", Huthig Buch Verlag, Heidelberg, pp. 54, 189, 241, 747, 775, 780, 108, 772 (1989).
Fiedler, Lexikon der Hilfsstoffe fur Pharmaize und angrenzende Gebiete, p. 390.
Chem. Abstr. 71:116481 (1989).
International Cosmetic Ingredient Dictionary, 5eme edition, vol. 1, p. 646 (1993).
Schrader, "Grundlagen und Rezepturen der Kosmetika", Huthig Buch Verlag, Heidelberg, (1989).
Cosmetics and Toiletries, vol. 106, p. 80 (1991).
Technisches Merkblatt Ultrahold 8, BASF AG, (1990).
Seifen–Ole–Fette–Wachse, 116, Jahrgang, Nr., pp. 130–137 (1990).

*Primary Examiner*—Raj Bawa
*Attorney, Agent, or Firm*—Nixon & Vanderhye, P.C.

[57] ABSTRACT

The present invention provides an aerosol hairspray lacquer containing a film forming resin, plasticizing agent, water and dimethylether.

8 Claims, No Drawings

AQUEOUS AEROSOL HAIR SPRAY

This is a continuation of Application Ser. No. 08/090,106, filed as PCT/FR92/01081, Nov. 20, 1992 published as WO93/09757, May 27, 1993, now abandoned.

This invention relates to an aqueous cosmetic composition in the form of an aerosol lacquer (hair spray) for holding hair and more particularly an aerosol hair spray with a high lacquering capacity.

BACKGROUND of INVENTION

Most aerosol hair sprays sold to date consist essentially of a "juice" containing a film-forming resin in alcoholic solution optionally with various cosmetic ingredients such as plasticisers, softeners, perfumes, oils, lubricants, lanoline, silicones, sun filters and also colorants. The "juice" is then packaged in an aerosol container pressurized by means of a chlorofluorocarbonated gas propellent such as the products sold under the name "Freons".

For ecological reasons the current tendency is systematically to replace chlorofluorocarbonated gas propellents in aerosol containers with propellents which present less risk to the ozone layer, like for example certain hydrocarbons such as propane, n-butane, isobutane or their mixtures in particular propane-butane mixtures or even dimethylether or a mixture of these gas propellents. For other reasons attempts have been made to replace the solvent of the film-forming polymer, either totally or partially, with water. The results have not been particularly convincing in that the lacquering capacity was not totally satisfactory.

DESCRIPTION of THE INVENTION

After considerable research it has now been established that it is possible to produce aqueous aerosol hair lacquers which have good cosmetic properties, namely an excellent lacquering capacity in particular. "Lacquering capacity" means the ability of the lacquer to hold the hair in the shape into which it has been styled.

According to the invention these results are essentially obtained by using certain plasticisers and certain film-forming polymers and also by using dimethylether as the propellent. This invention therefore provides an aqueous cosmetic composition in the form of a hair spray for holding hair containing:

(a) at least one synthetic film-forming resin, (b) at least one plasticiser in a proportion of at least 10% by weight relative to the weight of the film-forming resin, (c) water in which this film-forming resin and plasticiser are homogeneously dissolved and (d) dimethylether as propellent.

According to the invention, the film-forming resin is generally present in a proportion of between 0.1 and 20% and preferably between 3 and 10% by weight relative to the total weight of the composition.

It (the film-forming resin) must be soluble in water and also in water-dimethylether mixtures.

Among the synthetic film-forming resins that can be used in accordance with the invention, particular mention may be made of:

the vinyl acetate/vinyl tert butylbenzoate/crotonic acid terpolymers described in French patent 78.30596 (2.439.798), the N-octylacrylamide/methyl methacrylate/ hydroxypropyl methacrylate/acrylic acid/tert-butylamino-ethyl methacrylate copolymer sold by NATIONAL STARCH under the name "AMPHOMER LV-71", the vinylpyrrolidone/vinyl acetate copolymer sold by BASF under the name "LUVISKOL VA 64 Powder", the vinyl acetate/crotonic acid/vinyl neodecanoate terpolymer sold by NATIONAL STARCH under the name "RESINE 28-29-30", the acrylic acid/ethyl acrylate/N-tert-butylacrylamide terpolymer sold by BASF under the name "ULTRA-HOLD 8", the vinyl acetate/crotonic acid (90/10) copolymer sold by BASF under the name "LUVISET CA 66", the vinylcaprolactam/vinylpyrrolidone/dimethylamino ethyl methacrylate copolymer sold by GAF under the name "POLYMER ACP-1018".

In one particular embodiment, the synthetic film-forming resins can be used in the form of a mixture.

Among the synthetic resins named above, those which gave particularly interesting results are those described in French patent 78.30596 (2.439.798), the vinylpyrrolidone/vinyl acetate copolymer and the N-octylacrylamide/methyl methacrylate/ hydroxypropyl methacrylate/acrylic acid/tert-butylaminoethyl methacrylate copolymer.

Those copolymers above containing acrylic or crotonic acid units are generally used in their partially or totally neutralized form, the neutralisation being carried out with soda or potash or even by means of an alkanolamine such as 2-amino-2-methyl-1-propanol (AMP).

The copolymer which has led to particularly satisfactory aerosol lacquers is the vinyl acetate/vinyl tert-butylbenzoate/ crotonic acid (65/25/10) terpolymer the acid functions of which are neutralized by an alkanolamine, particularly AMP.

The plasticiser of the aerosol composition according to the invention is preferably present in a proportion of between 20 and 50% by weight relative to the weight of the resin.

As with the film-forming resin, the plasticiser must be soluble in water and in water-dimethylether mixtures. In addition, the plasticiser must be compatible with the resin, that is it must be able to be molecularly inserted in the film of resin without exudation occurring.

Among the particularly preferred plasticisers according to the invention, mention may be made of:

the glycol ethers described in the work "Industrial Solvents Handbook", Noyes Data Corporation, 2nd Ed., 1977—pp. 346 et seq. including the Carbitols sold by UNION CARBIDE, the Cellosolves sold by UNION CARBIDE and the Dowanols sold by the DOW CHEMICAL company. Of the Carbitols, mention may be made of: Carbitol or diethylene glycol ethylether, methylCarbitol or diethylene glycol methylether, butylCarbitol or diethylene glycol butylether and hexylCarbitol or diethyleneglycol hexylether.

Among the Cellosolves, mention can be made of: Cellosolve or ethylene glycol ethylether, butylCellosolve or ethylene glycol butylether, and hexylCellosolve or ethyleneglycol hexylether.

Of the Dowanols, mention can be made of Dowanol PM or propylene glycol methylether, Dowanol DPM or dipropylene glycol methylether, Dowanol TPM or tripropylene glycol methylether and Dowanol DM of diethylene glycol methylether.

Castor oil oxyethylenated with 40 moles of ethylene oxide such as that sold under the name "MULGOFEN EL-719" by RHONE POULENC, benzyl alcohol, alkyl citrates and their acetylated derivatives sold under the names "CITROFLEX" by MORFLEX and in particular triethyl citrate ("CITROFLEX-2") and tributyl acetyl citrate ("CITROFLEX-A4"), 1,3-butylene glycol, propylene carbonate, lauric acid diethanolamide sold under the name "MONA-MID 716"by MONA INDUSTRIES, and their mixtures.

In one particular method of carrying out the invention, the plasticiser is preferably a Dowanol, particularly Dowanol PM, Dowanol DPM and more particularly Dowanol TPM.

The solvent, namely water, is generally present in the aerosol composition in a proportion of between 9,8 and 89,8% by weight relative to the total weight of the composition and preferably between 50 and 70%.

The propellent, namely dimethylether, is generally present in a proportion of between 10 and 90% and preferably between 20 and 40% by weight relative to the total weight of the composition.

Even though the invention is not limited to a precise content of dimethylether, it is however preferred in accordance with the invention that this quantity be such that it results in a homogeneous liquid mixture.

According to the invention, it is desirable that in the aerosol container, the vapour pressure in the aerosol chamber be between about 2 and 5 bars at 20° C.

Hair sprays according to the invention can obviously contain other conventional ingredients such as softeners, perfumes, silicones, sun filters, colorants, preservatives, foam inhibitors, vitamins and also proteins.

The aerosol container in which the composition is packaged is of the conventional kind but can optionally be fitted with an extra gas inlet with a view to achieving a finer quality of spray.

Several examples of hair sprays according to the invention now follow by way of illustration and without in any way limiting the invention.

EXAMPLE 1

An aerosol hair lacquer is prepared by placing in an appropriate aerosol container, 6 g of the vinyl acetate/vinyl tert-butyl benzoate/crotonic acid (65/25/10 by weight) terpolymer in accordance with French patent N°78.30596 (2.439.798), that is 100% neutralized (according to the acid index) by the addition of 2-amino-2-methyl-1-propanol (AMP), 3 g of "Dowanol TPM" and the water required to make up 70 g.

Then using conventional techniques, 30 g of dimethylether are introduced and the fixing of the valve and hermetic sealing of the container are carried out (pressure 4,6 bars).

The valve can be of the type with an additional gas inlet with a view to obtaining a finer quality of spray.

By applying the lacquer to natural hair or sensitized hair, it was established that it has excellent lacquering capacity and does not cause stickiness on application and after drying.

EXAMPLE 2

Using the same procedure as described in example 1, an aerosol hair lacquer was prepared with the following composition:

N-octyl acrylamide/methyl methacrylate/hydroxypropyl methacrylate/tert-butyl-aminoethyl methacrylate copolymer sold under the name "AMPHOMER LV-71" by NATIONAL STARCH . . . 5 g AMP sufficient for 100% neutralization "DOWANOL TPM". . . 1,5 g Dimethylether . . . 30 g Water sufficient to make up to 100 g

EXAMPLE 3

Using the same procedure as described in example 1, an aerosol hair spray was prepared with the following composition:

Vinylpyrrolidone/vinyl acetate (60/40) copolymer sold under the name "LUVISKOL VA 64 Powder" by BASF . . . 6 g Benzyl alcohol . . . 2 g Dimethylether . . . 30 g Water sufficient to make up to 100 g

EXAMPLE 4

Using the same procedure as described in example 1, an aerosol hair spray fitted with a valve with an additional gas inlet was prepared with the following composition:

Vinyl acetate/crotonic acid/vinyl neodecanoate terpolymer sold under the name "RESIN 28-29-30 Quality E" by NATIONAL STARCH . . . 5 g AMP sufficient for 100% neutralization Triethyl citrate . . . 2,5 g Dimethylether . . . 30 g Water sufficient to make up to 100 g

EXAMPLE 5

Using the same procedure as described in example 1, an aerosol hair spray was prepared with the following composition:

Vinyl acetate/vinyl tert-butylbenzoate/crotonic acid (65/25/10) terpolymer described in French patent N°78.30596 (2.439.798) . . . 6 g AMP sufficient for 100% neutralization "Dowanol TPM". . . 1,8 g Dimethylether . . . 30 g Water sufficient to make up to 100 g

EXAMPLE 4

Using the same procedure as described in example 1, an aerosol hair spray was prepared with the following composition:

vinyl acetate/vinyl tert-butylbenzoate/crotonic acid (65/25/10) terpolymer described in French patent N°78.30596 (2.439.798) . . . 3 g Amp sufficient for 100% neutralization "Dowanol DPM" . . . 0,9 g Dimethylether . . . 35 g Perfume sufficient Water sufficient to make up to 100 g

We claim:

1. An aerosol hair spray lacquer comprising in an aerosol container, an aqueous aerosol hair spray composition consisting essentially of:

(a) a homogeneous liquid mixture consisting of water in an amount of 50 to 70% by weight based on the total weight of said composition and dimethylether as propellant in an amount of 20 to 40% by weight based on the total weight of said composition, (b) a synthetic film-forming resin in an amount of 3 to 20% by weight based on the total weight of said composition, and (c) a plasticizer in an amount of 10 to 50% by weight based on the weight of the synthetic film-forming resin, said film forming resin and said plasticizer being soluble in said homogeneous liquid mixture.

2. The lacquer according to claim 1, wherein the synthetic film-forming resin is selected from the group consisting of:

vinyl acetate/vinyl tert-butyl-benzoate/crotonic acid terpolymers,

N-octyl acrylamide/methyl methacrylate/hydroxypropyl methacrylate/acrylic acid/tert-butylamino-ethyl methacrylate copolymer, vinylpyrrolidone/vinyl acetate copolymer, vinyl acetate/crotonic acid/vinyl neodecanoate terpolymer, acrylic acid/ethyl acrylate/N-tert-butylacrylamide terpolymer, vinyl acetate/crotonic acid copolymer, vinylcaprolactam/vinylpyrrolidone/dimethylaminoethyl methacrylate polymer and mixtures thereof.

3. The lacquer according to claim 1, wherein the synthetic film-forming resin is vinyl acetate/vinyl tert-butyl-benzoate/crotonic acid (65/25/10) terpolymer neutralized with an alkanolamine.

4. The lacquer according to claim 2, wherein the synthetic film-forming resin is vinyl acetate/vinyl tert-butyl-benzoate/crotonic acid (65/25/10) terpolymer neutralized with an alkanolamine.

5. The lacquer according to claim 1, wherein the plasticizer is selected from the group consisting of:

glycol ethers, caster oil oxyethylenated with 40 moles of ethylene oxide, benzyl alcohol, alkyl citrates and their acetylated derivatives, 1,3-butylene glycol, propylene carbonate, lauric acid diethanolamine and mixtures thereof.

6. The lacquer according to claim 2, wherein the plasticizer is selected from the group consisting of:

glycol ethers, caster oil oxyethylenated with 40 moles of ethylene oxide, benzyl alcohol, alkyl citrates and their acetylated derivatives, 1,3-butylene glycol, propylene carbonate, lauric acid diethanolamine and mixtures thereof.

7. The lacquer according to claim 1, which further contains a conventional cosmetic ingredient selected from the group consisting of a softener, a perfume, a silicone, a sun filter, a colorant, a preservative, a foam inhibitor, a vitamin and a protein.

8. The lacquer according to claim 2, which further contains a conventional cosmetic ingredient selected from the group consisting of a softener, a perfume, a silicone, a sun filter, a colorant, a preservative, a foam inhibitor, a vitamin and a protein.

* * * * *